United States Patent
Jung, Jr. et al.

(10) Patent No.: US 6,645,422 B2
(45) Date of Patent: Nov. 11, 2003

(54) METHOD FOR MANUFACTURING A BALLOON FOR A DILATION CATHETER

(75) Inventors: Eugene J. Jung, Jr., San Diego, CA (US); Leo R. Roucher, Jr., Escondido, CA (US)

(73) Assignee: Jomed, Inc., Rancho Cordova, CA (US)

(*) Notice: Subject to any disclaimer, the term of this patent is extended or adjusted under 35 U.S.C. 154(b) by 42 days.

(21) Appl. No.: 09/918,599

(22) Filed: Jul. 27, 2001

(65) Prior Publication Data

US 2002/0041059 A1 Apr. 11, 2002

Related U.S. Application Data

(60) Continuation of application No. 09/114,565, filed on Jul. 13, 1998, now abandoned, which is a division of application No. 08/856,419, filed on May 14, 1997, now abandoned.

(51) Int. Cl.$^7$ ................ B29C 49/08; B29C 49/18
(52) U.S. Cl. ............... 264/530; 264/531; 264/532; 264/535; 264/573; 264/235; 264/346
(58) Field of Search ................ 264/529, 531, 264/532, 535, 573, 235, 346; 428/35.7, 36.9, 36.91, 36.92; 604/96, 915; 606/191, 192, 194

(56) References Cited

U.S. PATENT DOCUMENTS

| | | |
|---|---|---|
| 3,088,173 A | 5/1963 | Jones |
| 3,141,912 A | 7/1964 | Goldman et al. |
| 3,432,591 A | 3/1969 | Heffelfinger |
| 3,627,579 A | 12/1971 | Heffelfinger |
| 4,007,243 A | 2/1977 | Rupert ............ 264/530 |
| 4,093,484 A | 6/1978 | Harrison et al. |
| 4,141,364 A | 2/1979 | Schultze |
| 4,154,244 A | 5/1979 | Becker et al. |
| 4,155,974 A | 5/1979 | Valyi |
| 4,254,774 A | 3/1981 | Boretos |
| 4,456,000 A | 6/1984 | Schjeldahl et al. |
| 4,490,421 A | 12/1984 | Levy |
| 4,587,975 A | 5/1986 | Salo et al. |
| 4,646,742 A | 3/1987 | Packard et al. |
| 4,681,110 A | 7/1987 | Wiktor |
| 4,702,252 A | 10/1987 | Brooks et al. |
| 4,732,152 A | 3/1988 | Wallsten et al. |
| 4,733,665 A | 3/1988 | Palmaz |
| 4,739,762 A | 4/1988 | Palmaz |
| 4,744,366 A | 5/1988 | Jang |

(List continued on next page.)

FOREIGN PATENT DOCUMENTS

| | | |
|---|---|---|
| EP | 0 436 501 A1 | 7/1991 |
| EP | 0 592 885 A2 | 4/1994 |
| EP | 0 697 219 A2 | 2/1996 |
| WO | WO 96/12516 | 5/1996 |

*Primary Examiner*—Suzanne E. McDowell
(74) *Attorney, Agent, or Firm*—Fish & Neave; Nicola A. Pisano

(57) ABSTRACT

A method for forming a balloon for a dilation catheter is provided herein. The method includes the steps of: (i) positioning a tube in a preconditioned mold; (ii) expanding the tube in a preconditioned mold to form a parison; (iii) positioning the parison in a balloon mold; and (iv) expanding the parison within the balloon mold to form the balloon. Thus, the tube is initially expanded into a parison in the preconditioned mold. Subsequently, the parison is expanded into a balloon in the balloon mold. Because of this unique manufacturing process, polyester block copolymers can be formed into balloons. Some of these polyester block copolymers could not be formed into a balloon using prior art blow molding processes. The resulting balloon exhibits superior characteristics, including relatively thin and consistent walls, soft texture, low uninflated crossing profile, expansion in a predictable fashion, and good tensile strength.

16 Claims, 4 Drawing Sheets

U.S. PATENT DOCUMENTS

| | | |
|---|---|---|
| 4,776,337 A | 10/1988 | Palmaz |
| 4,795,458 A | 1/1989 | Regan |
| 4,800,882 A | 1/1989 | Gianturco |
| 4,878,906 A | 11/1989 | Lindemann et al. |
| 4,886,062 A | 12/1989 | Wiktor |
| 4,906,244 A | 3/1990 | Pinchuk et al. |
| 4,913,141 A | 4/1990 | Hillstead |
| 4,952,357 A | 8/1990 | Euteneuer |
| 4,969,458 A | 11/1990 | Wiktor |
| 5,108,415 A | 4/1992 | Pinchuk et al. |
| 5,156,612 A | 10/1992 | Pinchuk et al. |
| 5,236,659 A | 8/1993 | Pinchuk et al. |
| 5,304,197 A | 4/1994 | Pinchuk et al. |
| 5,334,146 A | 8/1994 | Ozasa |
| 5,344,401 A | 9/1994 | Radisch et al. |
| 5,356,591 A | 10/1994 | Pinchuk et al. |
| 5,403,538 A | 4/1995 | Maeda |
| 5,449,371 A | 9/1995 | Pinchuk et al. .............. 264/530 |
| 5,500,180 A * | 3/1996 | Anderson et al. ........... 264/532 |
| 5,554,120 A | 9/1996 | Chen et al. |
| 5,556,383 A | 9/1996 | Wang et al. ................... 604/96 |
| 5,565,523 A | 10/1996 | Chen et al. |
| 5,645,789 A | 7/1997 | Roucher, Jr. |
| 5,738,653 A | 4/1998 | Pinchuk et al. |
| 5,746,968 A | 5/1998 | Radisch, Jr. |
| 5,747,591 A | 5/1998 | Chen et al. |
| 5,792,415 A | 8/1998 | Hijlkema |
| 5,797,877 A | 8/1998 | Hamilton et al. |
| 5,879,369 A | 3/1999 | Ishida |

* cited by examiner

METHOD FOR MANUFACTURING A BALLOON FOR A DILATION CATHETER

REFERENCE TO RELATED APPLICATION

This Application is a continuation of U.S. application Ser. No. 09/114,565, filed Jul. 13, 1998, now abandoned, which is a Divisional Application of U.S. application Ser. No. 08/856,419 filed on May 14, 1997, now abandoned. The contents of U.S. application Ser. No. 08/856,419 filed on May 14, 1997 are incorporated herein by reference.

FIELD OF THE INVENTION

The present invention relates generally to a device for treating a blockage or stenosis in a vessel of a patient and a method for making the device. More specifically, the present invention relates to a balloon for a dilation catheter that is useful for performing medical dilation procedures such as angioplasty, and/or delivering a stent and a method for manufacturing the balloon.

BACKGROUND

It is well known that many medical complications are caused by a partial or total blockage or stenosis of a blood vessel in a patient. Depending on the location of the stenosis, the patient can experience cardiac arrest, stroke, or necrosis of tissues or organs.

Several procedures have been developed to treat stenoses, including angioplasty, incising and dilating the vessel, and stenting. These procedures typically utilize a dilation catheter having a balloon to dilate the vessel or deliver the stent. The desired size and physical characteristics of the balloon depend largely upon the size of the vessel and the intended use of the balloon.

Generally, balloons for dilation catheters are classified according to their "compliance" or expandability relative to other balloons. Typically, a balloon is rated as being either "compliant," "semi-compliant," or "non-compliant." A comprehensive definition of these terms is provided in U.S. Pat. No. 5,556,383, issued to Wang et al. and entitled "Block Copolymer Elastomer Catheter Balloons," the contents of which are incorporated herein by reference.

The physical characteristics of the balloon are primarily influenced by how the balloon is formed and by the material utilized in the balloon. Presently, most balloons are formed from a tube which is heated to above its glass transition temperature and radially expanded in a blow mold. Often, the tube is also subjected to an axial stretch so that the resulting balloon is bi-axially oriented.

Typically, non-compliant balloons are made from materials, such as polyethylene terephthalate. These non-compliant balloons are often relatively inflexible, are prone to develop pin holes, and the balloon does not rewrap well after inflation in the vessel. As a result thereof, these balloons are often difficult to remove from the delivery catheter. Further, if these balloons are used to position a stent in the vessel, the balloon frequently catches on the stent and repositions the stent in the vessel. On the other extreme, compliant balloons are typically made of materials, such as polyvinyl chlorides. However, compliant balloons often have a relatively low tensile strength, do not expand in a predictable fashion, and are subject to rupture during high pressure applications.

Recently, a number of semi-compliant balloons have been manufactured using materials, such as nylon and polyamide-polyether copolymers. These balloons exhibit many desirable characteristics including relatively thin walls, a soft texture, a low uninflated crossing profile, thermal stability, and good tensile strength. However, present semi-compliant balloons are not completely satisfactory, since these semi-compliant balloons are made by standard blow molding processes. For example, the wall thickness of a balloon manufactured by standard processes may be inconsistent and/or the balloon may have a compliance curve which is too steep or too flat. This can lead to unpredictable balloon inflation and/or over-inflation of the balloon in the vessel.

Further, it has been discovered that certain polymers, which exhibit desirable physical properties, can not be formed into a balloon using the present blow molding processes. In fact, these materials, namely certain polyester block copolymers will rupture during a typical blow molding process. Thus, it is believed that these polyester block copolymers have not been used for balloons.

In light of the above, it is an object of the present invention to provide a -balloon having improved physical characteristics for a wide variety of applications. It is another object of the present invention to provide a balloon having relatively thin, consistent walls, a soft texture, and a low uninflated crossing profile and a low rewrap profile after inflation in the vessel. Another object of the present invention is to provide a balloon which is thermally stable, semi-compliant, expands in a predictable fashion, and has improved tensile strength. Still another object of the present invention is to provide a balloon made from certain polyester block copolymers. Yet another object of the present invention is to provide a simple method for manufacturing a balloon which has greater control over the physical properties of the balloon.

SUMMARY

The present invention is directed to a balloon for a dilation catheter and a method for manufacturing a balloon which satisfy these objectives. The method for forming the balloon includes the steps of providing a tube, positioning the tube in a precondition mold, preconditioning the tube within the precondition mold to form a parison, positioning the parison in a balloon mold, and expanding the parison within the balloon mold to form the balloon.

As provided in detail below, the unique use of the precondition mold to form the parison from the tube provides for greater control over the dimensions and properties of the balloon. Further, certain materials which could not be formed into a balloon using prior art blow molding processes can be formed into a balloon using the process provided by the present invention.

As used herein, the term "parison" means and describes the preform which results from preconditioning the tube in the precondition mold.

The step of preconditioning of the tube to form the parison typically includes radially expanding the tube within the precondition mold to form the parison. Radial expansion of the tube can be accomplished by heating the tube to a first temperature ("T1") and pressurizing a lumen of the tube to a first pressure ("P1"). For the polyester-block copolymers provided herein, the first pressure P1 is at least approximately five hundred (500) psi.

The amount of preconditioning of the tube can vary according to the material utilized for the tube and the desired physical characteristics of the balloon. For example, the precondition mold can be sized so that the parison has a parison outer diameter which is at least over one (1) times larger than a tube outer diameter of the tube. Typically, however, the precondition mold is sized so that the tube radially expands within the preconditioning mold to form a parison having a parison outer diameter which is between approximately one and one-half (1.5) and two and one-half (2.5) times larger than the tube outer diameter. More specifically, for some of the embodiments provided herein, the precondition mold is sized so that the parison outer diameter is approximately one and seven-tenths (1.7) times larger than the tube outer diameter.

Preferably, the step of preconditioning of the tube to form the parison also includes axial stretching of the tube in the precondition mold. As provided herein, the tube can be axially stretched between approximately one and one-half (1.5) to two and one-half (2.5) an original tube length of the tube. This results in a highly oriented and work hardened parison which is ready to be formed into the balloon. Further, a wall thickness of the tube is substantially uniformly reduced within the precondition mold.

The balloon mold is typically sized so that parison can be radially expanded in the balloon mold to form a balloon having a balloon outer diameter which is between approximately one and one-half (1.5) and two and one-half (2.5) times larger than the parison outer diameter. More specifically, for some of the embodiments provided herein, the balloon mold is sized so that the parison is radially expanded into a balloon having a balloon outer diameter which is approximately two (2) times larger than the parison outer diameter.

Preferably, the parison is also axially stretched in the balloon mold so that the resulting balloon is highly bi-axially oriented. As provided herein, the parison can be axially stretched between approximately one (1.0) to one and one-half (1.5) times the parison length of the parison.

Additionally, it has been discovered that a balloon exhibiting superior physical characteristics, including a low crossing profile, a low rewrap profile, a soft texture, thermal stability, and semi-compliant expansion can be formed from polyester block copolymers. Specifically, it has been discovered that a superior balloon can be manufactured from a block copolymer which consists of an aromatic polyester hard segment and an aliphatic polyester soft segment. For example, an excellent balloon can be made from the copolymer sold under the trade name "Pelprene," by Toyobo, located in Osaka, Japan. This copolymer consists of an aromatic polyester hard segment and an aliphatic polyester soft segment. Additionally, it is believed that an excellent balloon can be made from the copolymer sold under the trade name "Hytrel," by DuPont, located in Wilmington, Del. This copolymer consists of a polybutylene terephthalate hard segment and a long chain of polyether glycol soft segment.

Importantly, the softening point for the specific polyester block copolymers identified above is very close to the melting point of the material. For these materials, little strength of the material is lost and little softening occurs during a standard blow mold process. With these materials, the pressure needed to initiate expansion of the tube is very high, typically, at least approximately five hundred (500) psi. With these polyester block copolymers, this would cause the tube to rupture prior to forming the balloon using a standard blow molding process. However, these materials can be formed into a balloon utilizing the unique process provided herein.

Additionally, the present invention relates to a device for manufacturing a balloon. The device includes a precondition mold suitable for expanding the tube into a parison and a balloon mold suitable for expanding the parison into a balloon.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
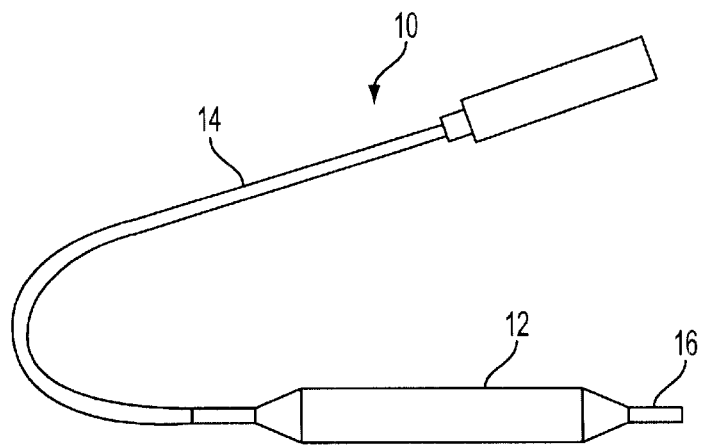
FIG. 1 is a side plan view of a dilation catheter having features of the present invention.

Referring initially to FIG. 1, the present invention is directed to a dilation catheter 10 which utilizes a balloon 12 to treat a vessel (not shown) of a patient (not shown). The balloon 12 provided herein, has improved physical characteristics, including a relatively high tensile strength, a relatively thin wall, a relatively low initial crossing profile, and a relatively low rewrap profile. Preferred embodiments of the balloon 12 provided herein are semi-compliant, soft, and expand in a predictable manner.

The improved physical characteristics of the balloon 12 are a result of the unique process used to manufacture the balloon 12 and the material used in forming the balloon 12. However, it is anticipated that the unique process can be used with other materials to form compliant or non-compliant balloons 12.

As shown in FIG. 1, the dilation catheter 10 includes a relatively thin, flexible length of tubing 14. The balloon 12 is positioned at the desired location along the length of tubing 14. In the embodiment shown in FIG. 1, the balloon is positioned proximate a distal tip 16 of the dilation catheter 10. The dilation catheter 10 is particularly useful for dilating a vessel, incising a vessel, and/or positioning a stent in a vessel of a patient. However, it is believed that the dilation catheter 10 and balloon 12 may be useful for other intravascular medical procedures.

Figure 2:
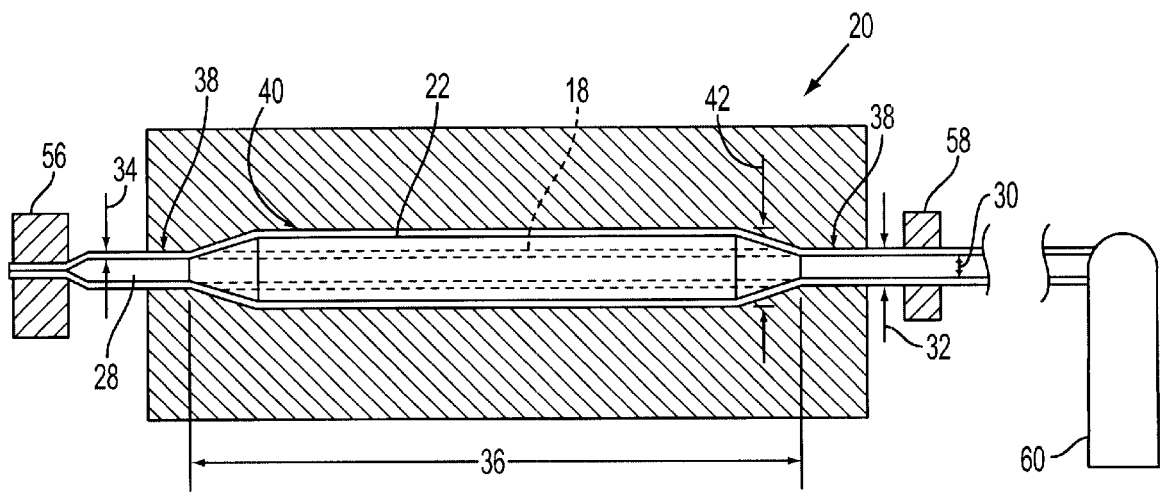
FIG. 2 is a cross-sectional view of a precondition mold, a parison and a tube (shown in phantom) having features of the present invention.
Figure 3:
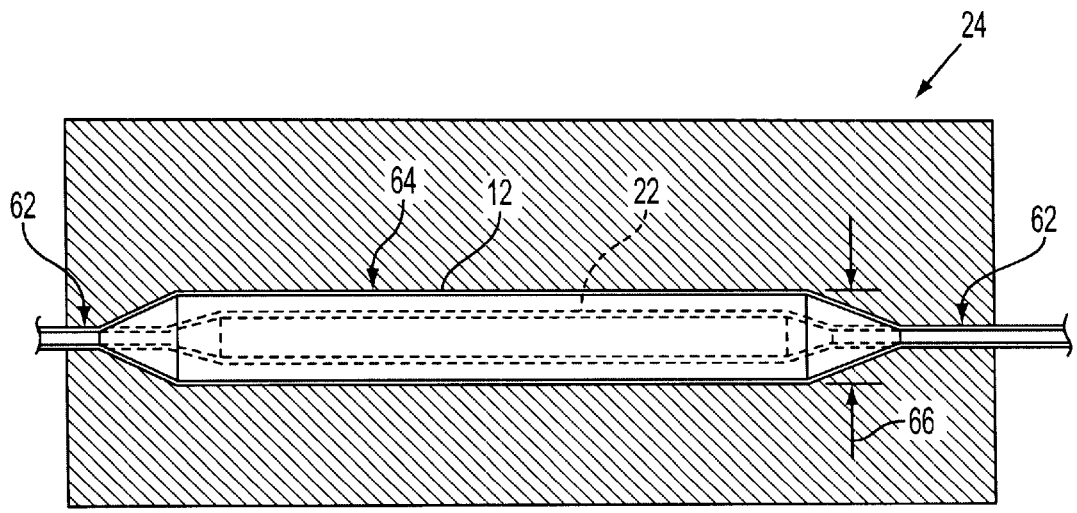
FIG. 3 is a cross-sectional view of a balloon mold, a balloon, and a parison (shown in phantom) having features of the present invention.

The balloon 12 is manufactured utilizing a unique process which allows for greater control over the physical characteristics of the balloon 12. Referring to FIGS. 2 and 3, as an overview, the unique process includes preconditioning a tube 18 (shown in phantom in FIG. 2) in a precondition mold 20 to form a parison 22 and subsequently expanding the parison 22 in a balloon mold 24 to form the balloon 12. Because the tube 18 is preconditioned in the precondition mold 20, there is greater control over the physical characteristics of the resulting balloon 12 and the balloon 12 can be manufactured from materials which would rupture during a normal, prior art, blow molding process.

For example, it has been discovered that an excellent, semi-compliant balloon 12 can be made from polyester block copolymers such as a polyester-polyester block copolymer consisting of an aromatic polyester as the hard segment and an aliphatic polyester as the soft segment. An example of a suitable block copolymer consisting of an aromatic polyester hard segment and an aliphatic polyester soft segment is manufactured by Toyobo, under the trade names "PELPRENE S6001," "PELPRENE S9001." Additionally, it is believed that other polyester block copolymers could be used for the balloon. For example, it is believed that the polymer manufactured by DuPont under the trade name "Hytrel" will make an excellent balloon 12.

Importantly, some polyester block copolymers such as "PELPRENE S6001" and "PELPRENE S9001" could not be manufactured using prior art balloon blow molding processes. This is because the pressure required to initiate expansion of the tube 18 is relatively high, i.e., at or above five hundred (500) psi. If a prior art blow molding process was used, the pressure required to initiate expansion would rupture the tube 18 prior to the balloon 12 expanding into its final configuration. With the process provided herein, the precondition mold 20 prevents radial expansion of the tube 18 prior to rupture of the tube 18.

Moreover, the unique manufacturing process provided above provides greater control over the physical characteristics of the balloon 12. Importantly, the dimensions, shape, and physical characteristics of the balloon 12 can be more closely varied and controlled utilizing the manufacturing process provided herein.

Additionally, it is believed that other materials such as PET, nylon, polymers, and other block copolymers can be used for the balloon with the unique process provided herein. With the use of alternate materials, it is believed that a compliant balloon 12, a non-compliant balloon 12, or a semi-compliant balloon 12 can manufactured using the process provided herein.

The tube 18 is typically extruded from the material using methods known by those skilled in the art. The tube 18 includes a lumen 28, a tube inner diameter 30, a tube outer diameter 32, a tube wall thickness 34, and a tube length 36 which can be varied according to the desired size and strength characteristics of the balloon 12.

The preconditioning mold 20 preconditions the tube 18 to create the parison 22. Basically, the precondition mold 20 is used to ready or precondition the tube 18 for expansion in the balloon mold 24. The required design of the precondition mold 20 depends upon the desired design of the balloon 12. In the embodiment shown in FIG. 2, the precondition mold 20 includes a pair of opposed precondition mold openings 38 and a precondition mold cavity 40 for forming the parison 22. The precondition mold openings 38 are each sized and shaped to receive the tube 18 and are typically right circular cylinder shaped.

The size and shape of the precondition mold cavity 40 varies according to the desired size and shape of the parison 22. In the embodiment shown in FIG. 2, the shape of the precondition mold cavity 40 is that of a pair of opposed, truncated right circular cones which are separated by a right circular cylinder. However, those skilled in the art will recognize that the precondition mold cavity 40 can have an alternate shape. For example, the opposed, truncated right circular cone could be replaced with a pair of opposed spherical segments (not shown).

The precondition mold cavity 40 restricts the expansion of the tube 18 and includes a precondition mold inner diameter ("PMID") 42 for restricting the expansion of the tube 18. The size of the precondition mold cavity 40 depends upon the size of balloon 12 to be manufactured, the material utilized, and the size of the tube 18. For example, in some instances, it may be beneficial for the PMID 42 to be only slightly larger, i.e., more than one (1) times larger than the tube outer diameter 32. Typically, however the precondition mold 20 has a PMID 42 which is approximately between one and one-half (1.5) to two and one half (2.5) times larger than the tube outer diameter 32. Therefore, for a tube 18 having a tube outer diameter 32 of about 0.035 inches, the precondition mold 20 has a PMID 42 of between approximately 0.052 inches and 0.0875 inches. However, it is anticipated that a PMID 42 larger than approximately two and one-half (2.5) times the tube outer diameter 32 may be useful.

Figure 4:
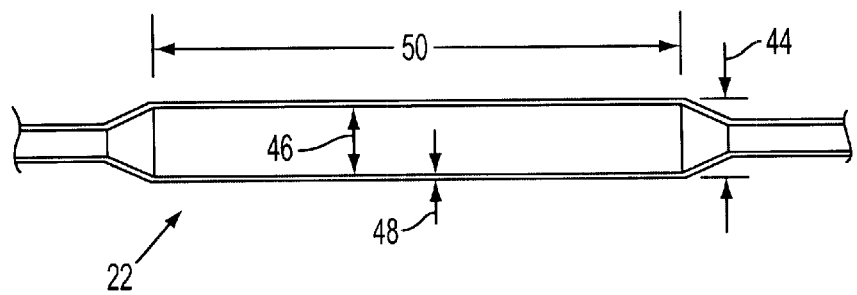
FIG. 4 is a cross-sectional view of a parison having features of the present invention.

Preferably, the tube 18 is axially stretched and radially expanded in the precondition mold 20 so that the parison 22 is bi-axially oriented. The amount of axial stretching and radial expansion can vary according to the requirements of the balloon 12. Referring to FIG. 4, the parison 22 that is formed from the tube 18 in the precondition mold 20 has a parison outer diameter 44, a parison inner diameter 46, a parison wall thickness 48, and a parison length 50.

Typically, the tube 18 is: (i) axially stretched between approximately one and one-half (1.5) to two and one-half (2.5) times the original tube length 36; and (ii) radially expanded so that the parison outer diameter 44 is between approximately one and one-half (1.5) to two and one-half (2.5) times larger than the tube outer diameter 32. The resulting parison 22 is highly oriented and has a parison wall thickness 48 which is approximately one-fourth (0.25) the tube wall thickness 34.

Referring back to FIG. 3, the balloon mold 24 is used to form the balloon 12 from the parison 22. Thus, the design of the balloon mold 24 also varies according to the desired design of the balloon 12. In the embodiment shown in FIG. 3, the balloon mold 24 includes a pair of opposed balloon mold openings 62 and a balloon mold cavity 64. The balloon mold openings 62 are generally right circular, cylinder shaped. The balloon mold cavity 64 forms the shape of the balloon 12. Accordingly, the balloon mold cavity 64 is shaped similar to the desired shape of the balloon 12. In the embodiment shown in FIG. 3, the shape of the balloon mold cavity 64 is that of a pair of opposed, truncated right circular cones which are separated by a right circular cylinder. However, those skilled in the art will recognize that the balloon mold cavity 64 could have an alternate shape.

The size of the balloon mold cavity 64 depends upon the desired size of balloon 12 to be manufactured. Typically, the balloon mold cavity 64 has a balloon mold inner diameter 66 ("BMID") which is approximately between one and one-half (1.5) to two and one-half (2.5) times larger than the PMID 42 of the precondition mold 20. For example, for a parison 22 having a parison outer diameter 44 of about 0.065 inches, the balloon mold 24 has a BMID 66 of between approximately 0.0975 inches and 0.1625 inches. However, it is anticipated that a BMID 66 which is less than approximately one and one-half (1.5) times the PMID 42 can be utilized. Similarly, it is also anticipated that a BMID 66 which is greater than approximately two and one-half (2.5) times the PMID 42 can be used.

Figure 5:
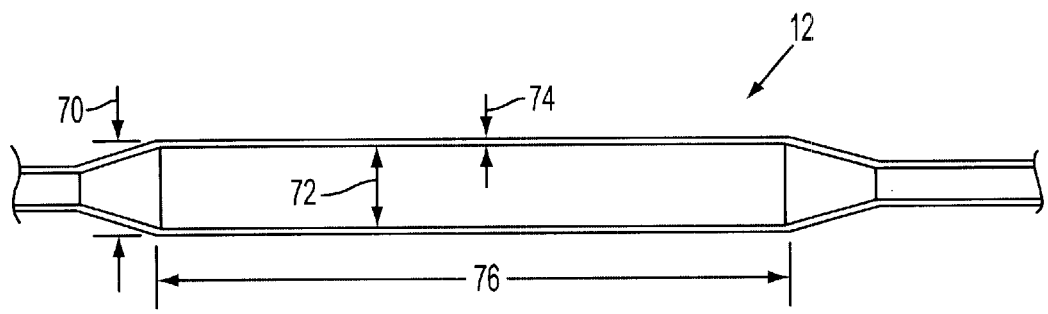
FIG. 5 is a cross-sectional view of a balloon having features of the present invention.

Typically, the parison 22 is axially stretched and radially expanded in the balloon mold 24 to form the balloon 12. The amount of axial stretch and radial expansion depends upon the requirements of the balloon 12. Referring to FIG. 5, the balloon 12 which is formed from the parison 22 in the balloon mold 24 has a balloon outer diameter 70, a balloon inner diameter 72, a balloon wall thickness 74 and a balloon length 76. Typically, the parison 22 is: (i) axially stretched between approximately one (1) to one and one-half (1.5) times longer than the parison length 50. The resulting balloon 12 is highly oriented and has a balloon wall thickness 74 which is approximately one-hird (⅓) the parison wall thickness 48.

To facilitate radial expansion and axial stretching, the precondition mold 20 and the balloon mold 24 are preferably heated to heat the tube 18 or the parison 22. This can be accomplished with a heating element (not shown) in the mold 20, 24 or by directing a hot fluid proximate the molds 20, 24. The axial stretching and the radial expansion typically occur when the material is at or above the glass transition temperature of the material which is being used.

Devices and methods for radially expanding and axially stretching a piece of tubing are well known by those skilled in the art. For example, as shown in FIG. 2, a first clamp 56 and a second clamp 58 can be used to grasp the tube 18 on each side of the precondition mold 20 and axially stretching the tube 18. The first clamp 56 also seals one (1) end of the tube 18 by compressing the tube 18. For axially stretching of the tube 18, the first clamp 56 and/or the second clamp 58 can be moved apart by a stepper motor (not shown).

Again referring to FIG. 2, the tube 18 can be radially expanded by releasing pressurized fluid from a container 60 into the lumen 28 of the tube 18. The pressurized fluid can be nitrogen gas, oxygen, or some other suitable fluid which is under pressure.

Typically, the axial stretching and the radial expansion occur substantially simultaneously. However, in certain instances, it may be beneficial for axial stretching to occur before the radial expansion or radial expansion to occur before the axial stretching.

Method of Manufacture

The following procedure describes how to form what is designed as a three millimeter (3 mm) by twenty millimeter (20 mm) balloon 12 from a polyester-polyester block copolymer sold under the trade name of "Pelprene S6001." It should be understood that the following procedure is merely provided as an example of a manufacturing process utilizing the precondition mold 20 and the balloon mold 24.

Figure 6:
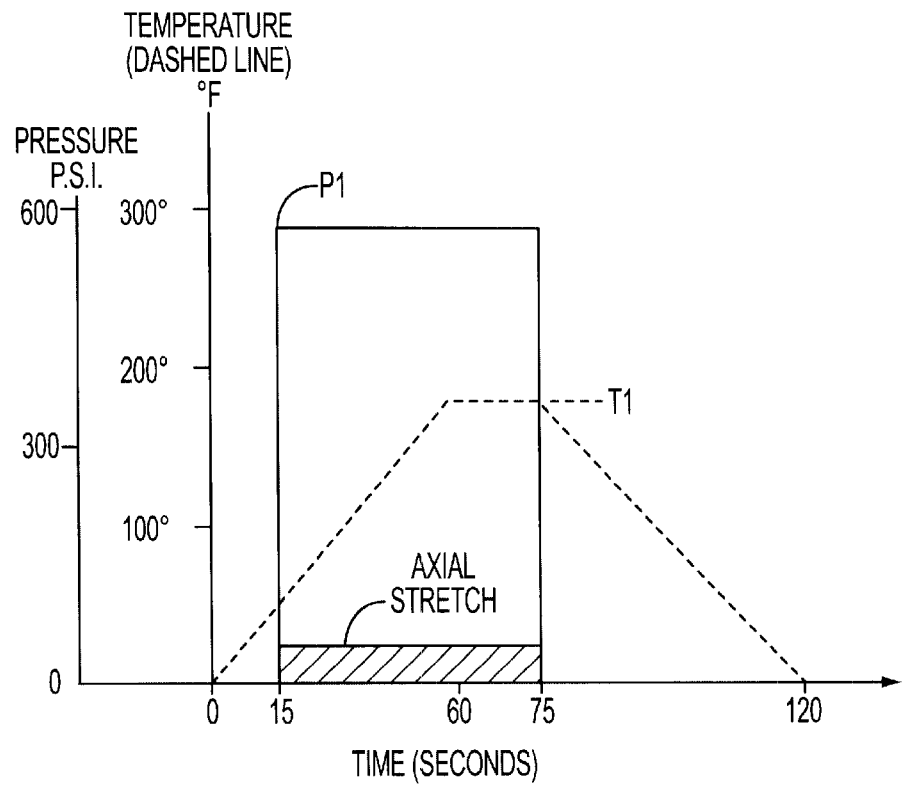
FIG. 6 is a graph which outlines one (1) example of the relationship between time, temperature, axial stretch, and pressure during the expansion of the tube in the precondition mold to form the parison.
Figure 7:
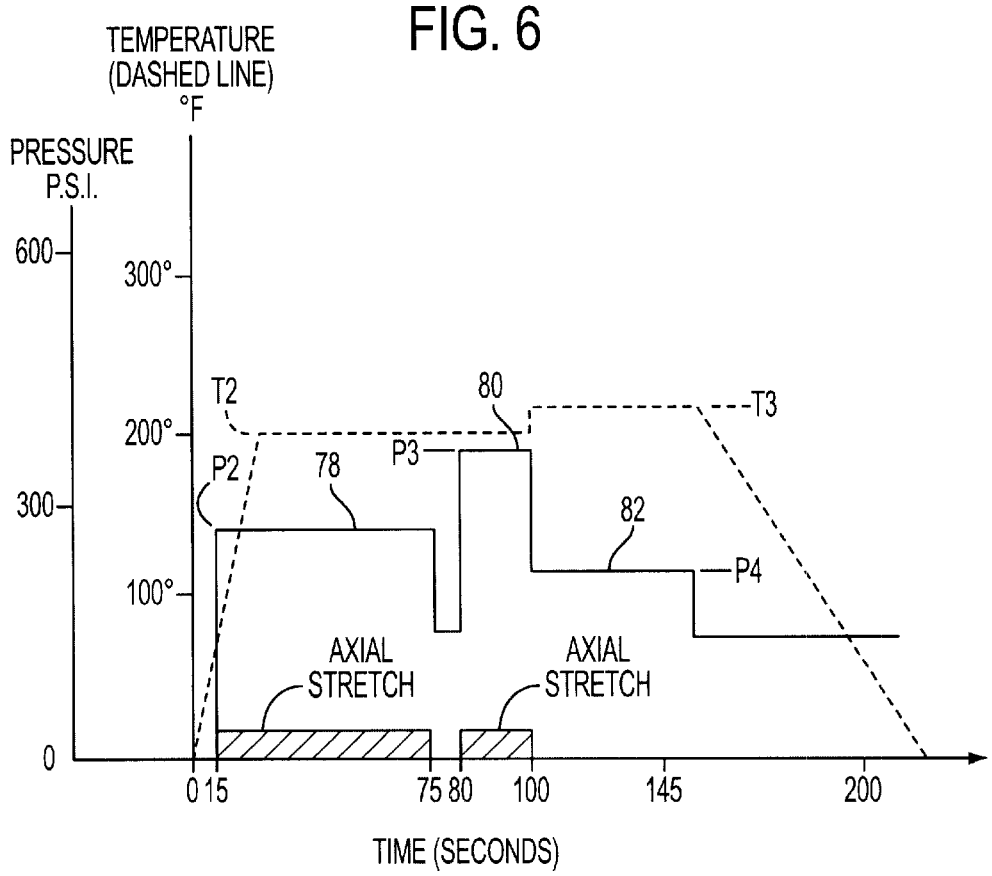
FIG. 7 is a graph which outlines one (1) example of the relationship between time, temperature, axial stretch, and pressure during the expansion of the parison in the balloon mold to form the balloon.

The relationship between time, temperature, axial stretch, and pressure, for this particular example, is provided in FIGS. 6 and 7. Importantly, the times, temperatures, pressures, and amount of axial stretching can be varied for a different material, a different size of balloon 12, or to alter characteristics of the balloon 12.

Initially, the tube 18 is extruded from the polyester-polyester block copolymer to form a tube 18 having a tube inner diameter 30 of approximately 0.017 inches, a tube outer diameter 32 of approximately 0.035 inches, a tube wall thickness 34 of approximately 0.009 inches, and a tube length 36 of approximately 2.6 centimeters. Subsequently, the tube 18 is placed inside the preconditioning mold 20. For this example, the preconditioning mold 20 has a PMID 42 which is approximately 0.06 inches. Referring to FIG. 6, the temperature of the tube 18 is ramped from approximately ambient temperature to a first temperature T1, which is between approximately one hundred and thirty degrees Fahrenheit (130° F.) to one hundred and eighty degrees Fahrenheit (180° F.) and preferably, approximately one hundred and fifty degrees Fahrenheit (150° F.). The increase in temperature only slightly softens the tube 18 made from the polyester-polyester block copolymer. After an initial, approximate fifteen (15) second delay, the tube 18 is radially expanded by applying a first pressure P1 to the lumen 28. The P1 is typically between approximately five hundred (500) to six hundred (600) psi. During this radial expansion, the tube 18 is also axially stretched approximately between one and one-half (1.5) to two and one-half (2.5) times the original tube length 36.

The axial stretch and pressure on the tube 18 in the precondition mold cavity 40 expands the tube 18 to form the parison 22. Importantly, the size of the precondition mold cavity 40 prevents the tube 18 from bursting during this procedure. Subsequently, the parison 22 is cooled until the temperature of the precondition mold 20 is below approximately one hundred degrees Fahrenheit (100° F.).

The result is a highly oriented, work hardened parison 22 having a parison outer diameter 44 of approximately 0.06 inches and a parison wall thickness 48 which is approximately one-fourth (0.25) times the original wall thickness.

Next, the parison 22 is positioned in the balloon mold 24. In this example, the balloon mold 24 has a BMID 66 which is approximately two (2) times larger than the PMID 42. In the balloon mold 24, the parison 22 is subjected to a first pressure cycle 78 and a second pressure cycle 80 to form the balloon 12.

During the first pressure cycle 78, the parison 22 is quickly heated from approximately ambient temperature to a second temperature ("T2"), which is between approximately one hundred and eighty degrees Fahrenheit (180° F.) to two hundred and ten degrees Fahrenheit (210° F.). After approximately a fifteen (15) second delay, the lumen 28 is pressurized to approximately a second pressure ("P2") which is between approximately two hundred and seventy (270) to three hundred and ten (310) psi and the parison 22 is axially stretched. After approximately seventy-five (75) seconds, the pressure is reduced to approximately one hundred and fifty (150) psi for approximately five (5) seconds.

Subsequently, in the second pressure cycle 80, the pressure in the lumen 28 is increased to a third pressure ("P3") which is between approximately three hundred and fifty (350) to five hundred and fifty (550) psi. The second pressure cycle 80 lasts approximately twenty (20) seconds.

At this time, the dimensions of the balloon 12 are substantially established and the balloon 12 is then subjected to the anneal cycle 82. The anneal cycle 82 prepares the balloon 12 for use by internally stabilizing the balloon 12 and relaxing the stress in the balloon 12. The anneal cycle 82 includes raising the temperature of the balloon mold 24 to a third temperature ("T3") which is between approximately one hundred and ninety degrees Fahrenheit (190° F.) to two hundred and twenty degrees Fahrenheit (220° F.) for forty-five (45) seconds and reducing the internal pressure on the lumen 28 to a fourth pressure ("P4") which is approximately one hundred and ninety (190) to two hundred and ten (210) psi.

Finally, the balloon 12 is cooled to ambient temperature. During the cooling of the balloon 12, the internal pressure on the lumen 28 is reduced to between approximately one hundred thirty (130) and one hundred eighty (180) psi and the balloon 12 is cooled until the temperature of the balloon 12 is below approximately one hundred degrees Fahrenheit (100° F.).

Figure 8:
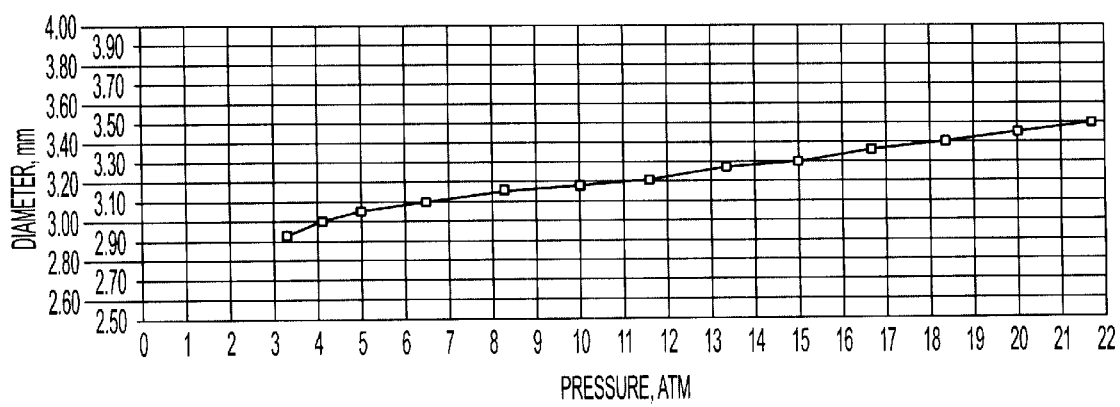
FIG. 8 is a graph which outlines the compliance curve for a balloon made in accordance with the present invention.

A compliance curve for a balloon 12 made in accordance with the procedure outlined above is provided in FIG. 8.

Importantly, the balloon 12 formed by this procedure has improved physical characteristics, such as being semi-compliant, soft, low crossing profile, and relatively high tensile strength.

Again, it should be noted that the above steps are merely exemplary. The temperatures, pressures, and amount of axial stretch can be varied according to the balloon material utilized and the desired physical characteristics of the dilation catheter 10.

While the particular balloon 12 and method for manufacturing a balloon 12, as herein shown and disclosed in detail, is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for forming a balloon, the method comprising:

providing a tube formed from a polyester block copolymer, said tube having a tube inner diameter and a tube outer diameter;

positioning the tube in a precondition mold, said precondition mold having a pair of opposed precondition mold openings;

expanding the tube within the precondition mold to form a parison, said parison having a parison outer diameter, said parison outer diameter being larger than said tube outer diameter;

positioning the parison in a balloon mold, the balloon mold having a balloon mold inner diameter which is larger than the precondition mold inner diameter, said balloon mold having a pair of opposed balloon mold openings; and expanding the parison within the balloon mold to form the balloon.

2. The method for forming a balloon of claim 1 wherein during formation of the balloon, expanding the tube includes heating the tube and pressurizing a lumen of the tube to a first pressure, which is at least approximately five hundred (500) psi.

3. The method for forming a balloon of claim 1 wherein the tube has an initial diameter of D and expanding the tube includes radially expanding the tube so that the parison has a parison outer diameter between 1.5D and 2.5D.

4. The method for forming a balloon of claim 1 wherein the tube has an initial length of L and expanding the tube includes axially stretching the tube to a length between 1.5L and 2.5L.

5. The method for forming a balloon of claim 1 wherein expanding the tube includes radially expanding the parison so that the balloon has a balloon outer diameter which is at least approximately one and one-half (1.5) times larger than a parison outer diameter of the parison.

6. The method for forming a balloon of claim 1 wherein providing a tube formed from a polyester block copolymer comprises providing a tube formed from an aromatic polyester hard segment and an aliphatic polyester soft segment.

7. The method for forming a balloon of claim 1 wherein providing a tube formed from a polyester block copolymer comprises providing a tube formed from a polybutylene terephthalate hard segment and a long chain of polyether glycol soft segment.

8. A method for forming a balloon for a dilatation catheter, the method comprising:

providing a tube formed from a polyester block copolymer and having a tube outer diameter and a lumen;

positioning the tube in a precondition mold, said precondition mold having an inner diameter which is between approximately one and one-half and approximately two and one-half times larger than the tube outer diameter;

heating the tube;

forming a parison by pressurizing said lumen of said tube;

positioning the parison in a balloon mold, said balloon mold having a balloon mold diameter at least five times larger than said tube inner diameter;

heating the parison in the balloon mold; and forming a balloon from the parison by pressurizing the lumen of the parison.

9. The method of claim 8 wherein forming a parison from the tube includes axially stretching the tube.

10. The method of claim 8 wherein forming a balloon from the parison includes axially stretching the parison.

11. The method of claim 8 wherein forming a balloon from the parison comprises pressurizing the lumen of the parison to at least approximately three hundred and fifty psi.

12. The method of claim 8 further comprising annealing the balloon in the balloon mold.

13. The method of claim 12 wherein annealing the balloon comprises annealing the balloon at a temperature at least approximately two hundred degrees Fahrenheit.

14. The method of claim 12 wherein annealing the balloon comprises annealing the balloon at a pressure of at least approximately two hundred psi.

15. The method of claim 8 wherein providing a tube formed from a polyester block copolymer comprises providing a tube formed from an aromatic polyester hard segment and an aliphatic polyester soft segment.

16. The method of claim 8 wherein providing a tube formed from a polyester block copolymer comprises providing a tube formed from a polybutylene terephthalate hard segment and a long chain of polyether glycol soft segment.

* * * * *